(12) United States Patent
Graf

(10) Patent No.: US 12,324,574 B2
(45) Date of Patent: *Jun. 10, 2025

(54) SURGICAL METHODS FOR THE TREATMENT OF PLANTAR PLATE INJURY

(71) Applicant: Sportwelding GmbH, Schlieren (CH)

(72) Inventor: Urs Graf, Zürich (CH)

(73) Assignee: SPORTWELDING GMBH, Schlieren (CH)

( * ) Notice: Subject to any disclaimer, the term of this patent is extended or adjusted under 35 U.S.C. 154(b) by 835 days.

This patent is subject to a terminal disclaimer.

(21) Appl. No.: 17/526,173

(22) Filed: Nov. 15, 2021

(65) Prior Publication Data

US 2022/0071617 A1 Mar. 10, 2022

Related U.S. Application Data

(63) Continuation-in-part of application No. 16/139,267, filed on Sep. 24, 2018, now Pat. No. 11,172,920.

(51) Int. Cl.
*A61B 17/04* (2006.01)
*A61B 17/00* (2006.01)
*A61F 2/08* (2006.01)

(52) U.S. Cl.
CPC ........ *A61B 17/0401* (2013.01); *A61F 2/0811* (2013.01); *A61B 2017/00955* (2013.01); *A61B 2017/0414* (2013.01); *A61B 2017/0458* (2013.01); *A61F 2002/0817* (2013.01)

(58) Field of Classification Search
CPC ............ A61B 17/0401; A61B 17/8861; A61B 17/8869; A61B 17/8872; A61F 2/0811; A61F 2002/0835; A61F 2002/0888
See application file for complete search history.

(56) References Cited

U.S. PATENT DOCUMENTS

| | | | |
|---|---|---|---|
| 9,060,763 | B2 | 6/2015 | Sengun |
| 2009/0062854 | A1 | 3/2009 | Kaiser et al. |
| 2009/0306776 | A1 | 12/2009 | Murray |
| 2012/0197296 | A1 | 8/2012 | Mayer et al. |
| 2013/0023988 | A1 | 1/2013 | Sinnott et al. |
| 2013/0178938 | A1 | 7/2013 | Fallin et al. |
| 2013/0184818 | A1 | 7/2013 | Coughlin et al. |
| 2014/0094911 | A1 | 4/2014 | Fallin et al. |
| 2017/0143551 | A1 | 5/2017 | Coleman |
| 2017/0156717 | A1 | 6/2017 | Triplett et al. |
| 2017/0224362 | A1 | 8/2017 | Hollis et al. |

(Continued)

FOREIGN PATENT DOCUMENTS

WO 2017/138917 8/2017

OTHER PUBLICATIONS

Xiao Huang et al., "Novel Porous Hydroxyapatite Prepared by Combining H2O2 Foaming with PU Sponge and Modified with PLGA and Bioactive Glass", Journal of Biomaterials Applications, Apr. 23, 2007, vol. 21, pp. 351-374, http:/jba.sagepub.com/.

(Continued)

*Primary Examiner* — Matthew J Lawson
(74) *Attorney, Agent, or Firm* — Rankin, Hill & Clark LLP

(57) ABSTRACT

Methods for the treatment of a ligament injury include the insertion of at least one suture anchor into a bone opening and anchoring the at least one suture anchor and thereafter threading two ends of a suture of at least one anchored suture anchor through the ligament and pulling the ligament to the bone with the opening and fixing the ligament to that bone by tying a knot in the suture.

10 Claims, 3 Drawing Sheets

(56) References Cited

U.S. PATENT DOCUMENTS

2017/0333101 A1 11/2017 Zeetser et al.
2019/0282246 A1 9/2019 Windram

OTHER PUBLICATIONS

C.A. Bailey et al., "Biomechanical Evaluation of a New Composite Bioresorbable Screw", The Journal of Hand Surgery, Apr. 2006, vol. 31B, No. 2, pp. 208-212.
S.M. Rea et al., "Bioactivity of ceramic-polymer composites with varied composition and surface topography", Journal of Materials Science; Materials in Medicine, (2004), vol. 15, pp. 997-1005, Cambridge, UK.
Liming Fang et al., "Processing and mechanical properties of HA/UHMWPE nanocomposites", Biomaterials (2006), vol. 27, pp. 3701-3707, Elsevier Ltd.

SURGICAL METHODS FOR THE TREATMENT OF PLANTAR PLATE INJURY

CROSS REFERENCE TO RELATED APPLICATION

This application is a continuation-in-part application of U.S. application Ser. No. 16/139,267 filed Sep. 24, 2018, which is expressly incorporated by reference.

BACKGROUND OF THE INVENTION

Field of the Invention

The invention is in the field of surgical procedures and concerns in particular methods for the treatment of ligament injury. The inventive methods refer mainly to the repair of severe injuries, where the ligament is pulled off the bone or is detached from the bone in order to correct the position of bones to each other and involves using of bone anchor to secure the ligament to the bone.

Description of Related Art

A ligament is a band or plate of fibrous connective tissue or fibrocartilage connecting bones or supporting muscles or organs. Ligaments are made of connective tissue including collagenous fibers. Articular ligaments connect one bone to another bone being part of joints within the skeletal part of the body. Ligaments cannot usually be regenerated naturally.

Ligaments vary in size, shape, orientation, and location, but have the same primary functions: limit the mobility of articulations, act as mechanical reinforcements. and provide joint stability. The consequence of an injured ligament can be instability of the joint and instability of a joint can over time resulting in damage to other structures in and around the joint such as wear of the cartilage and eventually osteoarthritis.

Ligaments have viscous as well as elastic properties. They gradually strain when under tension and return to their original shape when the tension is removed. However, the ligaments A ligament may be stretched, partially torn, or completely torn. The most common injury is a complete tear. Not all torn ligaments need surgery, but, if surgery is needed to stabilize the joint, the torn ligament may be repaired, which can be done through a variety of techniques and materials. One of these techniques is the replacement of the ligament with an artificial material.

A volar plate or ligament refers to ligament structures found in the human hand and foot. In the human hand, palmar plates are found in the metacarpophalangeal (MCP) and interphalangeal (IP) joints re-enforcing the palmar side of these joints. The MCPs involve the metacarpal bones and the proximal phalanges of the fingers. The proximal and distal interphalangeal (DIP) joints of the fingers are located distal to the MCP joints. The proximal interphalangeal (PIP) joints are formed by the articulation between the heads of the proximal phalanges and the bases of the middle phalanges. The DIP joints are formed through the articulation between the heads of the middle phalanges and the bases of the distal phalanges. The capsule at each interphalangeal (IP) joint is strengthened by radial and ulnar collateral ligaments and a palmar plate. If the palmar plate is injured during hyperextension, it can scar and lead to flexion contractures. Avulsion fractures of the volar plate are very common injuries, often resulting from sporting injuries and usually involving the middle and ring fingers. The palmar approach is indicated mainly for volar plate avulsion fractures of the base of the middle phalanx. Thereby a volar plate is attached, using either a pullout suture, or at least two anchor sutures. Extensive comminution of the palmar margin is the main indication for volar plate arthroplasty of the PIP joint. Therefore, a criss-cross stitch (Bunnell) in each side of the volar plate is used on both sides and the free ends are fixed using drill holes (through holes) in the ulnar.

The plantar plate is a fibro-cartilaginous ligament on the underside (plantar) of the foot, running along the first joint of each toe. Its purpose is to protect the head of the metatarsal from pressure and injury and to prevent the over extension of the toe by hindering the joint from bending upward beyond the normal range of motion. It also keeps each toe stabilized to prevent them from drifting out of their normal alignment. A plantar plate injury refers to damage to said strong supporting ligament of a toe. Injury to the plantar plate is usually caused by overuse, such as from running; obesity; or wearing high heeled shoes too often. Damage to the plantar plate can be chronic and include a lengthening or partial tear of the ligament. The most serious form of plantar plate injury is a total rupture of the plate, when the ligament tears completely and leaves no link between the metatarsals and phalanges. Severe damage to the Plantar Plate is frequent in professional sports. Most commonly the 2nd toe is involved, but any toe can be damaged. A chronic plantar plate injury is very different than an acute injury. Here the plantar plate (ligament) will have micro-tears and stretch out over time. A chronic injury can occur from a trauma where the initial plantar plate tear was undiagnosed—this is best considered a non-healing injury. Alternatively, a chronic injury of the plantar plate may occur from biomechanical imbalance to the foot. Chronic plantar plate injury can develop into a hammer toe (toe contracture). Hammer toe is a deformity of the toe that affects the alignment of the bones adjacent to the proximal interphalangeal (PIP) joint. Hammer toe can cause pain and can lead to difficulty in walking or wearing shoes. A hammer toe can often result in an open sore or wound on the foot. In some instances, surgery may be required to correct the deformity. A turf toe injury refers to hyperextension injury to the hallux metatarsophalangeal (MTP) joint which may include a complete rupture of the plantar structures of the hallux MTP joint.

To fix this problem, surgeons have historically transferred tendons from the bottom of the toe to the top of the toe to pull the toe back down to the floor. The 'flexor to extensor tendon transfer' is still considered a very good operation and is still used today. An alternative to the flexor-extensor tendon transfer is to directly repair the plantar plate. Surgical procedure for a plantar plate repair can be done either from a plantar or dorsal approach. The dorsal approach has been found to include many advantages over the plantar approach, especially in that a patient can bear weight on the foot after about 48 hours of surgery and that the correction tends to be solid. The dorsal approach can reduce the risk of compromising the principal blood supply to the affected digits and with the plantar approach the level of complications, such as scar formation is greater than with the dorsal approach. In addition, if an osteotomy is necessary, the dorsal approach enables the surgeon to repair the plantar plate and the collateral ligaments and conduct osteotomy through the same incision. The repair is performed with sutures to re-approximate or advance the plantar plate back to the base of the toe. Part of the operation may involve shortening the toe a few millimeters with a 'Weil Osteotomy.' Shortening the toe allows the surgeon to gain access to the plantar plate and also decreases tension and forefoot pressure post-operatively.

Employing a dorsal approach and combining Weil's osteotomy is well known in the art and usually includes a number of steps including: performing a Weil's osteotomy allowing the capital fragment to be recessed under the metatarsal; digital distraction by a distraction clamp over K-wires; assessing the plantar plate and repairing same by passing a suture through the plantar plate; followed by the step of repairing the plantar plate back to the proximal phalanx. The success of this procedure depends greatly on the ability to place the suture in the plantar plate correctly. This often proves fairly difficult because the dorsal approach results in soft tissue limitations meaning the space is confined. The confined space further necessitates retraction of soft tissue. A plethora of methods and tools have been developed to facilitate the placing of this suture in a convenient and accurate manner. The most common is by employing the various devices described in US 2013/0184818.

Current systems such as the one described in WO 2017/138917 A1 require at least one tunnel or through bore to be drilled into the phalangeal bone of the treated joint in order to achieve fixation of the plantar plate. The suture strands need to get through said tunnels, which is difficult to handle and often requires the operation site to be opened wide to allow access.

In attaching a ligament to bone, various surgical techniques are available, including suture anchors and fixation through bone tunnels (transosseous tunnels). The creation of bone tunnels is relatively complicated, often requiring an extensive exposure to identify the margins of the tunnels. The process is time-consuming and fraught with complications, which include poor tunnel placement and fracture of the overlying bone bridge. After creation of tunnels, sutures must be passed through the tunnels. Finally, the procedure can be compromised if the bone bridge above the tunnel breaks, resulting in loss of fixation. A brittle bone may not last when tying a suture after passing the bone tunnel. In addition, an interarticular bone tunnel may widen associated with sclerosis of the tunnel wall.

SUMMARY OF THE INVENTION

It is accordingly an object of the present invention to provide a ligament repair method with which the above disadvantages could at least partially be overcome or alleviated and/or to provide a more useful alternative to the known methods. In particular, it is an object to provide a method for the treatment of ligament injury without using transosseous tunnels.

This object is achieved by the invention as is defined in the patent claims.

The invention provides further a surgical method for the treatment of ligament injury and techniques for complete ligament repair. The present invention refers to methods for reconstruction of the ligament through a dorsal, lateral or medial incision, restoring the normal alignment of the injured joint. The access depends on the joint and the ligament injured. A medial or lateral incision is suitable for a collateral ligament. Thereby healing complications should be minimized, e.g. by minimizing trauma to the bone and the surrounding tissue. The method for the treatment of ligament injury according to the present invention includes the steps of a) exposing a joint including the injured ligament, ii) distracting the joint to expose the injured ligament, iii) inserting at least one suture anchor into a bone opening being a blind hole and anchoring the at least one suture anchor, iv) threading two ends of a suture of the at least one anchored suture anchor through the ligament, v) pulling the ligament to the bone with the opening, and fixing the ligament to that bone by tying a knot in the suture between the bone and the dorsal side of the ligament. This new method is possible using at least one suture anchor including a material having thermoplastic properties and being anchored in the bone opening with the aid of vibratory energy used for in situ liquefaction of the material having thermoplastic properties. In one embodiment only one suture anchor is suitable for the repair of the ligament. The suture can be attached to the at least one suture anchor before its fixation in the bone and at least before step iv) is carried out.

Using the methods of the invention it is possible to secure the suture anchor in the bone, with the free end(s) of the suture extending out of the bone, before the suture is (are) passed through the ligament. Another advantage of the method of the present invention is that the two ends of the suture may be passed only once through the ligament in a direction from outside of the joint towards the joint or the bone. Thereafter the suture ends are fastened with a knot, which may be any common surgical knot. The knot can be placed between the bone and the ligament. The knot may be located below the bone opening. Therefore, the length of the suture is very short. Compared to common techniques the suture is about ten-times shorter. This increases the stiffness of the construct and avoids the so called "bungee effect". The injured ligament may be a volar plate, in particular a palmar plate, a collateral ligament of the interphalangeal joints of the foot, a collateral ligament of metatarsophalangeal joints, a first intermetacarpal ligament, a syndesmosis ligament or a plantar calcaneonavicular ligament. The at least one anchor may be placed outside the articular surface and also the knot is preferably placed outside the articular surface.

It is also possible to use two suture anchors. Therefore, one embodiment refers to a surgical method for the treatment of ligament injury and techniques for complete ligament repair including the step: inserting at least two suture anchors, each into a separate bone opening and anchoring the at least two suture anchors, wherein the at least two suture anchors include the at least one suture anchor, threading two ends of a suture of each anchored suture anchor through the ligament, pulling the ligament to the bone with the opening and fix the ligament to that bone by tying a knot in each suture.

The invention provides further a surgical method for the treatment of plantar plate injury and techniques for complete plantar plate repair. The present invention refers to methods for reconstruction of the plantar plate through a dorsal, lateral or medial incision, restoring the normal alignment of the metatarsophalangeal joint. A medial access is possible in case of the big toe and a lateral access in case of the little toe. Thereby healing complications should be minimized, e.g. by minimizing trauma to the bone and the surrounding tissue. The method for the treatment of plantar plate injury according to the present invention includes the steps of: i) performing a longitudinal dorsal, lateral or medial incision to expose a metatarsophalangeal joint, ii) distracting the metatarsophalangeal joint to expose a plantar plate, iii) inserting at least one suture anchor into a bone opening and anchoring the at least one suture anchor, iv) threading two ends of a suture of at least one anchored suture anchor through the plantar plate, and v) pulling the plantar plate to the bone with the opening and fix the soft tissue to that bone by tying a knot in the suture.

One main difference of the present invention refers to the sequence of the steps used. So far it is necessary to thread the suture through the plantar plate and the bone tunnel and subsequently set the anchor or place the implant for fixation of the suture. With the present invention it is possible to set the anchor firstly and secondly thread the suture of the anchored anchor through the plantar plate and pull it to the bone. Therefore, it is possible to insert a suture anchor with previously attached sutures.

Using the methods of the invention it is for the first time possible during plantar plate repair to lock the suture to the bone, with the free end(s) of the suture extending out of the bone, before the suture is (are) passed through the plantar plate. Therefore one aspect of the present invention refers to methods for treatment of plantar plate injury according to the present invention including the steps of: i) performing a longitudinal dorsal, lateral or medial incision to expose a metatarsophalangeal joint, ii) hereafter distracting the metatarsophalangeal joint to expose a plantar plate, iii) subsequently inserting at least one suture anchor into a bone opening and anchoring the at least one suture anchor, iv) after this threading two ends of a suture of at least one anchored suture anchor through the plantar plate, and v) hereafter pulling the plantar plate to the bone with the opening and fix the soft tissue to that bone by tying a knot in the suture.

Another advantage of the method of the present invention is that the two ends of the suture may be passed through the plantar plate in a plantar to dorsal direction. Thereafter the sutures are fastened with a knot, which may be any common surgical knot. The knot can be placed between the phalangeal bone and the dorsal side of the plantar plate. The knot may be located below the bone opening. Therefore, the length of the suture is very short. Compared to common techniques the suture is about ten-times shorter. This increases the stiffness of the construct and avoids the so called "bungee effect". It is proposed that a long suture and its elasticity within the bone tunnel causes micro-movements of the reattached plantar plate compromising healing, besides problems like abrasion of the suture in the tunnel. Under load, the "bungee effect" may also allow gaping of the plantar plate off the bone, which could even be a cause of failure.

The method of the present invention is especially suitable for the treatment of a hammer toe or a turf toe as well as a deformity of the proximal interphalangeal joint of the little toe. There are some small differences depending on the toe to be treated. One refers to the incision. The metatarsophalangeal joint of the big toe and the little toe may be exposed using a medial incision or a dual incision for medial and lateral access. Therefore one embodiment of the invention refers to the method wherein the metatarsophalangeal joint is the joint of the second, third or fourth toe. In this case the method includes the step: performing a longitudinal dorsal incision to expose a metatarsophalangeal joint. Another embodiment of the invention refers to the method, wherein the metatarsophalangeal joint is the joint of the big or little toe and includes: performing a longitudinal medial incision to expose a metatarsophalangeal joint.

For treatment of the metatarsophalangeal joint of the big toe it may be suitable to use two anchors. These anchors are set side by side and dorsal of the articulate surface on the proximal phalanx. Therefore one embodiment of the invention refers to a method wherein the metatarsophalangeal joint is the joint of the big toe and the method includes: performing a longitudinal medial incision to expose a metatarsophalangeal joint, distracting the metatarsophalangeal joint to expose a plantar plate, inserting at least two suture anchors into a bone opening and anchoring the at least one suture anchor, threading two ends of a suture of each anchored suture anchor through the plantar plate, pulling the plantar plate to the bone with the opening and fix the soft tissue to that bone by tying a knot in the suture.

It is possible to use a wide range of known suture anchors within the method of the invention. The suture anchor should be rather small and holding one suture with two open ends. Nevertheless, it is advantageously the at least one suture anchor used within the method of the present invention includes a material having thermoplastic properties. The suture anchor having thermoplastic properties may be anchored in the bone opening with the aid of vibratory energy used for in situ liquefaction of the material having thermoplastic properties.

A suture anchor is a small device used during surgical procedures to attach soft tissue, such as ligaments and tendons, to bone. This may be achieved by tying one end of a suture to soft tissue and the other end to a device which "anchors" the suture to the bone. Suture anchors typically are implanted into the bone with suture attached to the anchor. Various techniques of suture attachment have been developed. Most commonly a suture anchor includes an elongate body to which a suture has been attached using an eyelet or the like. Thereby the eyelet-is a hole or a loop in the anchor to through which the suture passes. Suture anchors may be made of titanium metal, polyetheretherketone thermoplastic, or biodegradable absorbable material. There are many suture anchors on the market today. In general, they can be classified as screw-in or and non-screw-in anchors, commonly using an interference fit. A suture is typically an elongate flexible filament, but may take a variety as different thread or thread-like structures, including without limitation fibers, lines, and the like. A suture may be a homogeneous or heterogeneous, and may also include a single filament or a composite suture, such as a two or more twisted or woven filaments. In addition, a suture may be made from a wide array of absorbable (i.e., metabolized by the body) or non-absorbable materials known in the art.

Materials having thermoplastic properties suitable for the suture anchor used in the method according to the invention are thermoplastic polymers, e.g.: resorbable or degradable polymers such as polymers based on lactic and/or glycolic acid (PLA, PLLA, PGA, PLGA etc.) or polyhydroxy alkanoates (PHA), polycaprolactone (PCL), polysaccharides, polydioxanes (PD) polyanhydrides, polypeptides or corresponding copolymers or composite materials containing the named polymers as a component; or non-resorbable or non-degradable polymers such as polyolefines (e.g. polyethylene), polyacrylates, polymetacrylates, polycarbonates, polyamides, polyester, polyurethanes, polysulfones, polyarylketones, polyimides, polyphenylsulfides or liquid crystal polymers LCPs, polyacetales, halogenated polymers, in particular halogenated polyolefines, polyphenylensulfides, polysulfones, polyethers or equivalent copolymers or composite materials containing the named polymers as a component.

One embodiment of the present invention refers to the method for the treatment of plantar plate injury according to the present invention, wherein the at least one anchor is fully made of a bio-degradable material. Specific embodiments of bio-degradable materials are Polylactides like LR706 PLD-LLA 70/30, R208 PLDLA 50/50, L210S, and PLLA 100% L, all of Böhringer.

Specific embodiments of non-degradable materials are Polyetherketone (PEEK Optima, Grades 450 and 150, Invibio Ltd), Polyetherimide, Polyamide 12, Polyamide11, Polyamide 6, Polyamide 66, Polycarbonate, Polymethylmethacrylate, Polyoxymethylene, or polycarbonate-urethane (e.g. Bionate by DSM, in particular types 65D and 75D).

The material having thermoplastic properties may further contain foreign phases or compounds serving further functions. In particular, the thermoplastic material may be strengthened by admixed fibers or whiskers (e.g. of calcium phosphate ceramics or glasses) and such represent a composite material. The material having thermoplastic properties may further contain components which expand or dissolve (create pores) in situ (e.g. polyesters, polysaccharides, hydrogels, sodium phosphates), compounds which render the implant opaque and therewith visible for X-ray, or compounds to be released in situ and having a therapeutic effect, e.g. promotion of healing and regeneration (e.g. growth factors, antibiotics, inflammation inhibitors or buffers such as sodium phosphate or calcium carbonate against adverse effects of acidic decomposition). If the thermoplastic material is resorbable, release of such compounds is delayed. If the device is to be anchored not with the aid of vibration energy but with the aid of electromagnetic radiation, the liquefiable material having thermoplastic properties may locally contain compounds (particlulate or molecular) which are capable of absorbing such radiation of a specific frequency range (in particular of the visible or infrared frequency range), e.g. calcium phosphates, calcium carbonates, sodium phosphates, titanium oxide, mica, saturated fatty acids, polysaccharides, glucose or mixtures thereof.

Fillers used may include degradable, osseostimulative fillers to be used in degradable polymers, including: B-Tricalciumphosphate (TCP), Hydroxyapatite (HA, <90% crystallinity); or mixtures of TCP, HA, DHCPBioglasses (see Wintermantel). Osseo-integration stimulating fillers that are only partially or hardly degradable, for non-degradable polymers include: Bioglasses, Hydroxyapatite (>90% cristallinity), HAPEX®, see SM Rea et al., J Mater Sci Mater Med. 2004 September; 15(9): 997-1005; for hydroxyapatite see also L. Fang et al., Biomaterials 2006 July; 27(20): 3701-7, M. Huang et al., J Mater Sci Mater Med 2003 July; 14(7): 655-60, and W. Bonfield and E. Tanner, Materials World 1997 January; 5 no. 1:18-20. Embodiments of bioactive fillers and their discussion can for example be found in X. Huang and X. Miao, J Biomater App. 2007 April; 21(4): 351-74), J A Juhasz et al. Biomaterials, 2004 March; 25(6): 949-55. Particulate filler types include: coarse type: 5-20 μm (contents, entially 10-25% by volume), sub-micron (nanofillers as from precipitation, preferentially plate like aspect ratio >10, 10-50 nm, contents 0.5 to 5% by volume). Experiments show that liquefaction with the aid of ultrasonic vibration energy allows filling the thermoplastic polymer to a relatively high degree without impairing the capability of the liquefied material to penetrate structures as e.g. the trabecular structure of viable cancellous bone.

The suture anchor used in the method according to the invention may consist of any suitable material or material combination (e.g. polymer, metal, ceramic, glass) which material may be bio-resorbable or not bio-resorbable and liquefiable or not liquefiable. Non-bioresorbable or non-biodegradable such materials may include surfaces equipped for furthering osseointegration (e.g. per se known surface structures or coatings) where in contact with the bone tissue, in particular if the material of the suture anchor is bio-resorbable or bio-degradable and therefore the anchoring function needs to be gradually taken over by osseointegration. Good results have e.g. been achieved with suture anchors of polylactic acid (PLA) filled with Hydroxyapatite or calciumphosphates, in particular of PLLA filled with 60% tricalciumphosphate or PDLLA 70%/30% (70% L and 30% D/L) filled with 30% biphasic calciumphosphate, combined with suture anchors of PLDLLA 70%/30% (70% L and 30% D/L), as available from Böhringer as LR706. In the case of the suture anchor being integrated in the suture anchor, the two items may consist of the same material, e.g. the above named PLLA filled with 60% tricalciumphosphate or PDLLA 70%/30% (70% L and 30% D/L) filled with 30% biphasic calciumphosphate, wherein the filler content may be smaller in areas in which the material is to be liquefied than in other areas.

If the suture anchor is to be forced into the hard tissue, it needs to include at least in its distal end a material having a corresponding mechanical strength which is dependent on the mechanical resistance expected of the hard tissue into which the anchor is to be forced. If such resistance is relatively high (forcing through cortical bone or hard and dense cancellous bone) the distal end of the anchor includes e.g. a metal such as e.g. titanium or a titanium alloy, a ceramic material such as e.g. sintered calcium phosphate (e.g. hydroxyapatite) or engineering ceramics (e.g. zirkonia, alumina) or PEEK or a comparable high temperature resistant polymer, while other anchor portions are made e.g. of a biocomposite material such as e.g. the above mentioned filled polylactides or of one of the other above mentioned thermoplastic polymers. Alternatively such distal end of the anchor may include a hard and possibly abrasive coating e.g. made by plasma sprayed deposition of calcium phosphate or titanium powder on PEEK or polylactide or biocomposites.

The energy used for the liquefaction of the material having thermoplastic properties is preferably mechanical vibration, in particular ultrasonic vibration generated by a vibration source (e.g. piezoelectric vibration generator possibly including a booster to which the tool is coupled) and the anchoring tool is suitable for transmission of the vibration from its proximal end to its distal face, preferably such that the distal face vibrates with a maximal longitudinal amplitude. For the in situ liquefaction the vibration is transmitted from the distal tool face to the suture anchor and transformed into friction heat in places where the suture anchor is held against a counter element (hard tissue and/or part of the suture anchor). It is possible also to activate the anchoring tool to vibrate in a radial or in a rotational direction.

Alternatively, the energy source may be a laser, preferably emitting laser light in the visible or infrared frequency range and the anchoring tool is equipped for transmitting this light to its distal end, preferably via glass fiber. For the in situ liquefaction the laser light is transmitted into the suture anchor and absorbed where liquefaction is desired, wherein the material of the suture anchor may contain particles or substances effecting such absorption.

As anchoring of the suture anchor is only little dependent on the quality of the hard tissue, the method according to the invention is suitable in particular for fixating a suture anchor in hard tissue of an only small mechanical stability, wherein this is largely true even if the first fixating step is chosen to result in only a very weak fixation in such hard tissue.

In one aspect of the invention, a method for plantar plate repair includes exposing a metatarsophalangeal joint, wherein the metatarsophalangeal joint includes a metatarsal, a proximal phalanx, a plantar plate, and a flexor tendon; detaching a plantar plate from the proximal phalanx and the flexor tendon; distracting the metatarsophalangeal joint; forming one bone opening in the proximal phalanx; providing a suture anchor and anchoring said suture anchor in the bone opening; threading two free suture ends of the suture anchor through a distal portion of the plantar plate; advancing the plantar plate until it rests against the proximal phalanx; reposition of the proximal phalanx; tensioning the suture; tying a knot in the suture, the knot resting against the dorsal side of the plantar plate; and closing the exposure of the metatarsophalangeal joint.

One embodiment refers to a method for the treatment of plantar plate injury according to the present invention, wherein threading two ends of a suture through the plantar plate includes passing the suture in a plantar to dorsal direction. Another embodiment refers to a method for the treatment of plantar plate injury according to the present invention, wherein tying a knot in the suture includes tying the knot near a plantar phalangeal cortex of the phalangeal bone resting against the dorsal side of the plantar plate. It is therefore possible that the knot is placed outside the articular surface. Therefore, the impingement risk is minimized.

When threading the ends of a suture through the plantar plate one can use a suture passing instrument such as a Mini Scorpion DX™. The suture passes from the anchor to the adjoining plantar plate only (see FIG. 4), thus it is very short. One advantage of the present method is said very short suture which provides great tensile strength as well as stiffness and therefore allows only little play.

The bone opening formed in the proximal phalanx may be a blind hole. The bone opening or blind hole can be placed outside the articular surface, respectively outside the metatarsophalangeal joint or only at the periphery of the articular surface. The bone opening may be placed adjoining to the plantar plate insertion. In more detail it may be placed proximal to the insertion side but outside the articular surface. In other words, the bone opening may be placed within the curvature (proximal extremities) of the proximal phalanx. Consequently, it is possible that the at least one anchor is placed outside the articulating sliding surfaces. The bone opening should form an angle with the tangent running through the plantar plate insertion side of 30 to 60°.

The inventive method avoids transosseous holes which and is thus, less invasive. It is possible to maintain greater bone strength versus systems that use multiple bone tunnels. Furthermore, to pass a suture through a bone tunnel and retrieval of the suture at or very near the plantar plate, can be very tedious and time consuming in the operating room. Within the present invention the suture anchor can easily be placed by exposing the joint and allows for a smaller incision. In addition, the bone tunnel is not completely filled with the suture and there is a space left in the bone tunnel. A space remaining in a bone tunnel causes the following subcutaneous hemorrhage, pain, and swelling due to bleeding from bone marrow in a bone tunnel, and therefore the risk of infection increases. Compared with common surgical methods for repairing plantar plate injury the inventive method causes less trauma.

Inserting at least one suture anchor into a bone opening and anchoring the at least one suture anchor may include the following steps: Introducing the suture anchor into the bone opening with the suture having two freely accessible ends by pushing the suture anchor into the bone opening using a tool and by simultaneously or later transmitting energy via the tool to the suture anchor thereby liquefying material of the suture anchor having thermoplastic properties.

Using the inventive method there is no need to pull the anchor tight to determine whether full insertion has been reached. One embodiment refers to a method for the treatment of plantar plate injury according to the present invention, wherein there is no need to pull the at least one anchor tight.

The method according to the invention may include creating a Weil osteotomy of a distal epiphysis of the metatarsal; temporarily fixing a distal capital fragment of the metatarsal to a plantar aspect of the distal epiphysis of the metatarsal; removing the temporary fixation of the distal capital fragment of the metatarsal to the distal epiphysis of the metatarsal; reducing the distal capital fragment of the metatarsal against the distal epiphysis of the metatarsal; and securing the distal capital fragment of the metatarsal to the distal epiphysis of the metatarsal. Therefore, one aspect of the present invention refers to a method for the treatment of plantar plate injury including a Weil osteotomy of a distal epiphysis of the metatarsal of the exposed metatarsophalangeal joint.

The method of the present invention is particularly suitable for the treatment of collateral ligament injuries (stabilization after rupture and reconstruction of collateral ligaments), such as a skier's thumb (UCL tear), reconstruction of the collateral ligament during surgery to treat a hallux varus deformity, or reconstruction of the collateral ligament in regard to Stainsby procedure (resection(al) arthroplasty in a metatarsophalangeal joint). The invention provides a surgical method for the treatment of an injury of a collateral ligament. The present invention refers to methods for reconstruction of the collateral ligament through a dorsal, lateral or medial incision, restoring the normal alignment and/or the stability of the affected joint. The method for the treatment of a collateral ligament injury according to the present invention includes the steps of: i) performing an incision to expose an affected joint, ii) distracting the joint to expose the collateral ligament, iii) inserting at least one suture anchor into a bone opening and anchoring the at least one suture anchor, iv) threading two ends of a suture of at least one anchored suture anchor through the collateral ligament, and v) approximating the collateral ligament to the reattachment site (bone opening) and inserting the sutures ends through the ligament, each with one stitch, and knotting them. The ligaments are locked to the bone with the free end(s) of a suture extending out of the bone. The two ends of the suture may be passed through the ligament in a lateral to medial direction. Thereafter the sutures are fastened with a knot, which may be any common surgical knot. The knot can be placed between the bone and the medial side of the collateral ligament. The knot may be located adjacent to the bone opening.

The invention provides a surgical method for the treatment of palmar plate injury and techniques for complete palmar plate repair. The present invention refers to methods for reconstruction of the palmar plate through a dorsal, lateral or medial incision, restoring the normal alignment of the metatarsophalangeal joint. A medial access is possible in case of the thumb and a lateral access in case of the little finger. The method for the treatment of palmar plate injury according to the present invention includes the steps of: i) performing a longitudinal dorsal, lateral or medial incision to expose a metatarsophalangeal joint, ii) distracting the metatarsophalangeal joint to expose a palmar plate, iii) inserting at least one suture anchor into a bone opening and anchoring the at least one suture anchor, iv) threading two ends of a suture of at least one anchored suture anchor through the palmar plate, and v) pulling the palmar plate to the bone with the opening and fix the soft tissue to that bone by tying a knot in the suture. Using the methods of the invention it is for the first time possible during palmar plate repair to lock the suture to the bone, with the free end(s) of the suture extending out of the bone, before the suture is (are) passed through the palmar plate. It is one advantage of the method of the present invention that the two ends of the suture may be passed through the palmar plate in a palmar to dorsal direction. Thereafter the sutures are fastened with a knot, which may be any common surgical knot. The knot can be placed between the phalangeal bone and the dorsal side of the palmar plate. The knot may be located below the bone opening.

DETAILED DESCRIPTION OF THE INVENTION

The following more detailed description of the embodiments of the method is a representative of exemplary embodiments of the technology, wherein similar parts are designated by same numerals throughout. Standard medical planes of reference and descriptive terminology are employed in this specification. A sagittal plane divides a body into right and left portions. A transverse plane divides a body into superior and inferior portions. Anterior means toward the front of the body. Posterior means toward the back of the body. Superior means toward the head. Inferior means toward the feet. Medial means toward the midline of the body. Lateral means away from the midline of the body. Axial means toward a central axis of the body. Proximal means toward the trunk, or, in the case of an inanimate object, toward a user. Distal means away from the trunk, or, in the case of an inanimate object, away from a user. Dorsal means toward the top of the foot. Plantar means toward the sole of the foot. Ipsilateral means on the same side of the body. Contralateral means on the opposite side of the body.

Figure 1:
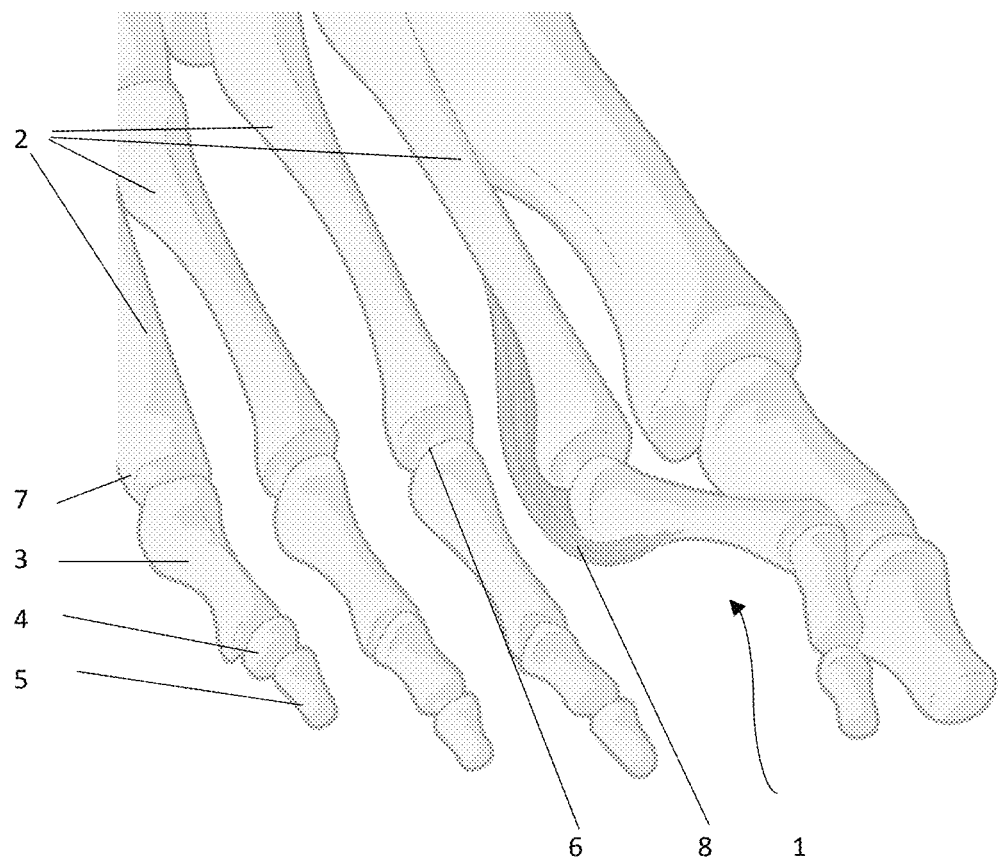
FIG. 1 shows a schematic overview of the foot with a hammer toe or contracted toe as a deformity of the proximal interphalangeal joint of the second toe causing it to be permanently bent.
Figure 2:
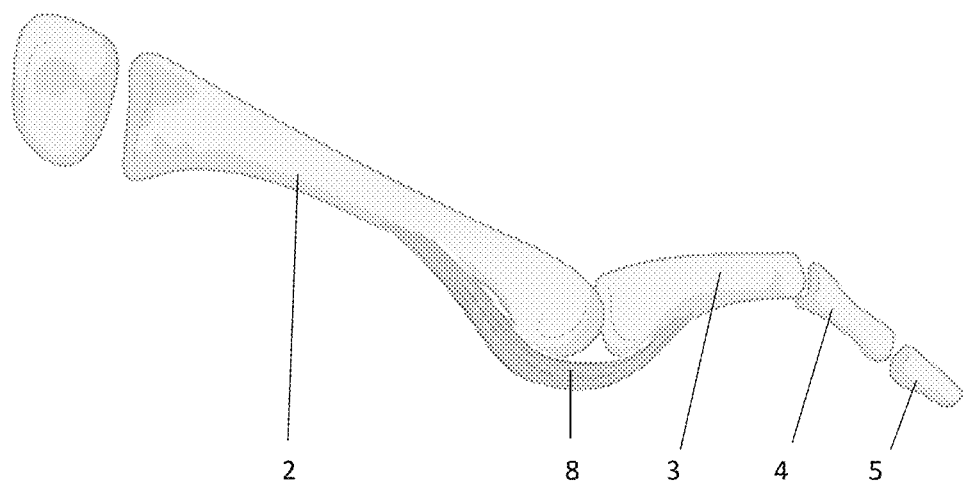
FIG. 2 shows side view of a deformed proximal interphalangeal joint of the second toe causing it to be permanently bent.

FIGS. 1 and 2 illustrate the most important anatomical structures of a foot with a hammer toe (1) or contracted toe as deformity of the metatarsophalangeal joint (6) of the second toe causing it to be permanently bent. The metatarsophalangeal joints (6) are the joints between the metatarsal bones (2) of the foot and the proximal phalanges (3) of the toes. Thee great toe only has two phalanx bones (proximal and distal phalanges) and only one interphalangeal joint, which is often abbreviated as the "IP joint." The rest of the toes each have three phalanx bones, the proximal (3), middle (4), and distal phalanges (5), so they have two interphalangeal joints. The plantar plate (8) is a rectangular, fibrocartilaginous structure overlying plantar aspects of metatarsophalangeal joints and is formed from distal parts of plantar aponeurosis and plantar aspects of metatarsophalangeal joint capsules.

Figure 3:
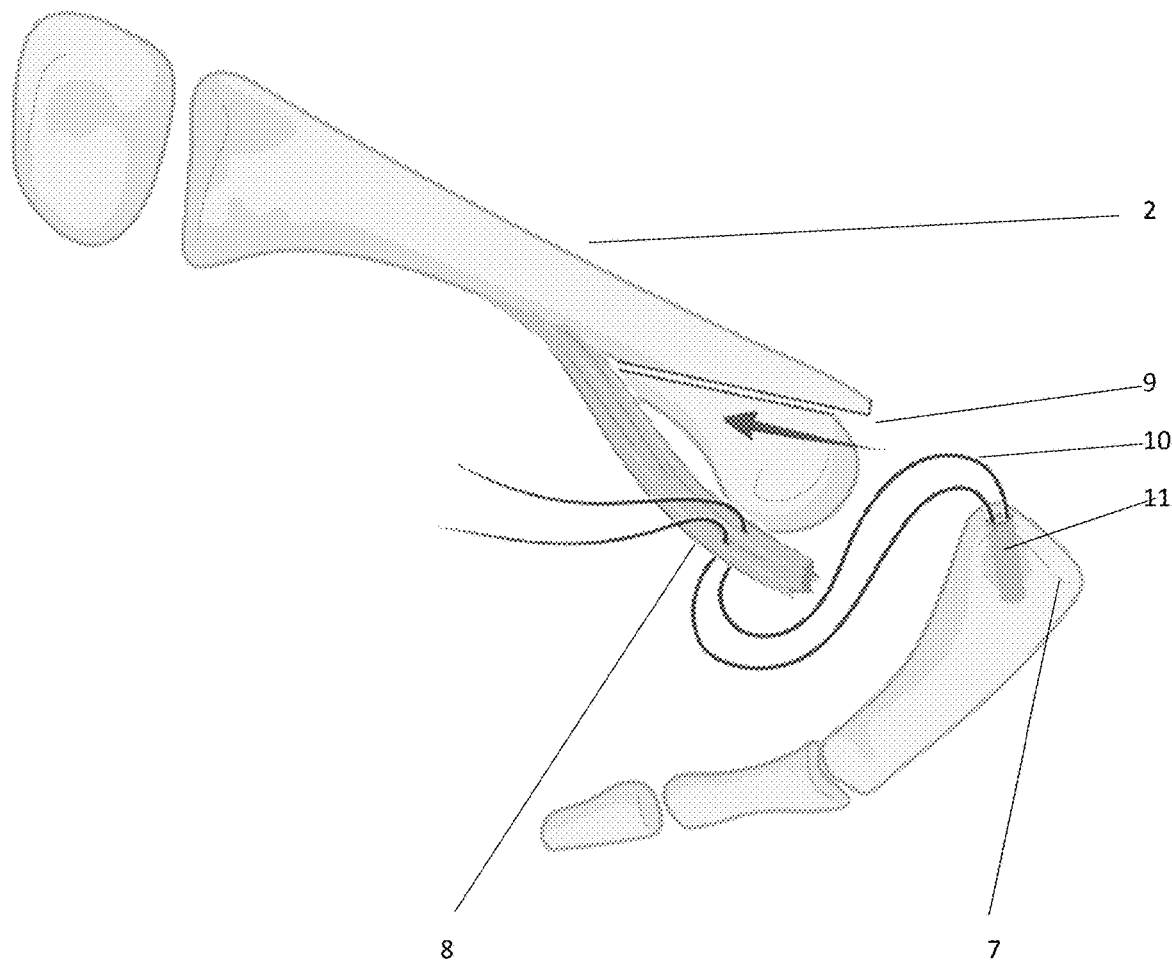
FIG. 3 shows first steps of the method according to the invention including insertion and anchoring of a suture anchor and threading two ends of a suture of through the plantar plate.
Figure 4:
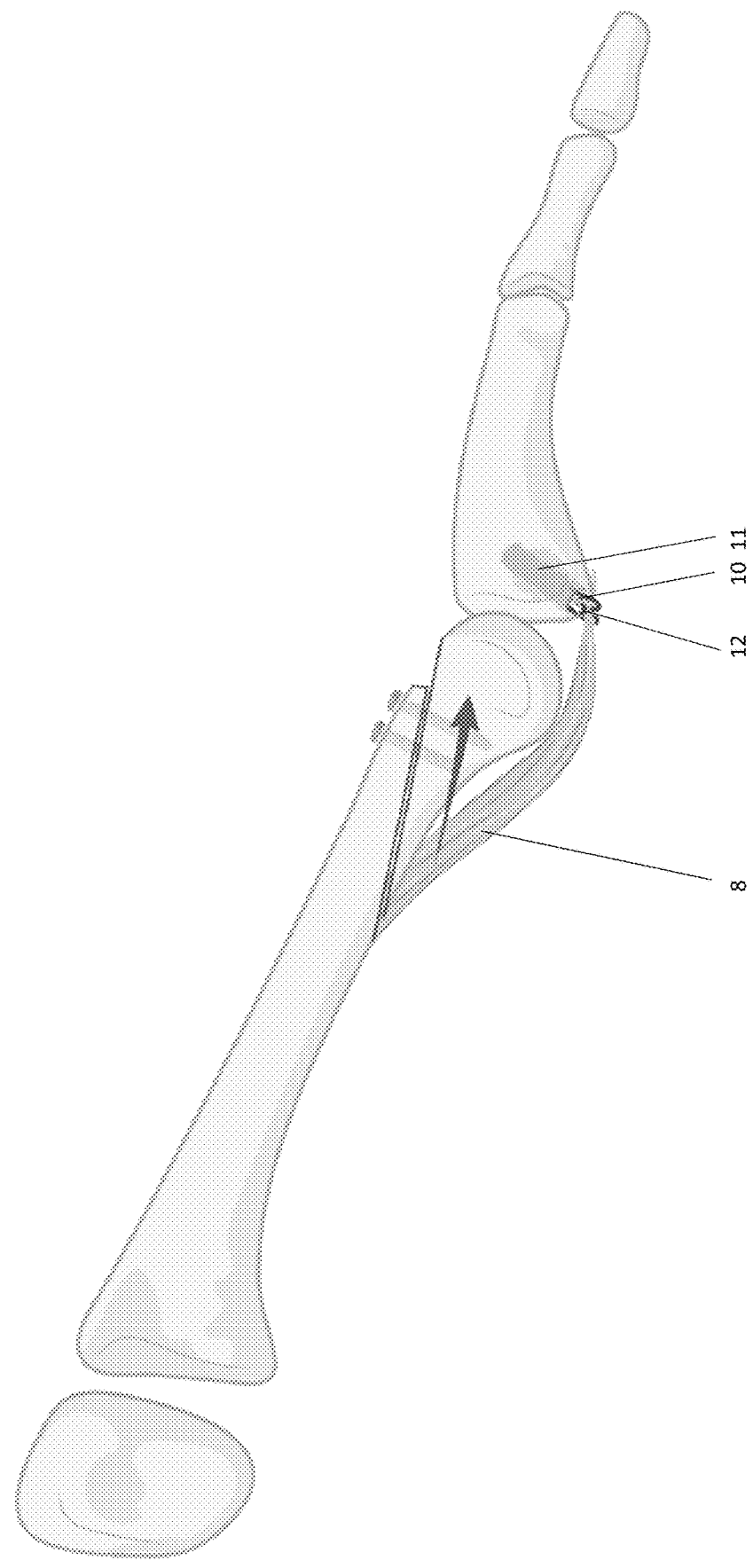
FIG. 4 shows additional steps of the method according to the invention including repositioning the metatarsal head.

An exemplary method of plantar plate repair employing a dorsal approach and combining a Weil osteotomy in accordance with the present invention is shown in the FIGS. 3 and 4. A dorsal longitudinal incision is centered over the second metatarsophalangeal joint (6). A longitudinal capsulotomy is performed to expose the affected second metatarsophalangeal joint (6). A partial collateral ligament release off of the proximal phalanx (3) of the metatarsophalangeal joint (6) may improve visualization. A metatarsal shortening osteotomy (Weil osteotomy, 9) is performed using a sagittal saw. The saw cut is made parallel to the plantar aspect of the foot. The capital fragment is provisionally pushed proximally and may be fixed with a temporary vertical Kirschner wire (k-wire), to hold it in a retracted position. A plantar plate distractor may be placed and spread to expose the plantar plate (8). The most common tear patterns of the plantar plate are partial and complete distal transverse tears at the distal insertion of the plantar plate. In case of partial transverse tear on should make the partial tear a complete tear as close as possible to the insertion of the plantar plate to the proximal phalanx (3). This reflects the plantar plate off the flexor tendon sheath.

A blind hole is created dorsal of the articulate surface on the proximal phalanx (plantar rim of the proximal phalanx). Thereafter a suture anchor (11) is inserted in the blind hole and anchored in a way that two free ends of the suture are accessible.

The distal plantar plate (8) is transfixed proximal to the transverse tear using for example a small curved needle or a suture passing instrument to pass the two free ends of the suture (10) through the plantar plate (8). As shown in FIG. 3 passing the suture (10) through the plantar plate occurs preferably, plantar to dorsal. When passed through the plantar plate, the suture tis pulled tight, thereby advancing the plantar plate onto the proximal phalanx (3). The suture (10) is then tied between the plantar plate (8) and the proximal phalanx (3). After removal of the joint distractor the phalanx is plantar flexed.

The distal plantar edge of the proximal phalanx may be roughened with a burr or curette to prepare a surface for re-implantation of the plantar plate. The metatarsal shortening (Weil) osteotomy (9) is moved to anatomic positioning, typically with 1-2 mm of shortening at the osteotomy site. It is fixed in optimal position with one or two small screws or k-wire. Wound closure is performed.

The inventor used the inventive method to treat some patients successfully. The fact that the suture does not have to be passed through bone tunnels meant considerable time savings around 15 to 20 minutes less per operation. In addition, he could observe that for the patients this new method involves less swelling and pain. This causes better and faster wound healing for all patients treated so far.

In addition it is suitable to use very small anchors such as the SportWelding® Fiji Anchor®. This together with the short suture and the less traumatic approach enable to treat also plantar plate injuries of the third to fifth toe using the methods of the present invention.

The invention claimed is:
1. A method for the treatment of ligament injury comprising the following steps:
   i) exposing a joint comprising the injured ligament,
   ii) after step i), distracting the joint to expose the injured ligament, iii) after step ii), inserting at least one suture anchor into a bone opening, which is a blind hole, and anchoring the at least one suture anchor in the bone opening,
iv) after step iii), threading two ends of a suture of the at least one anchored suture anchor through the injured ligament,
v) after step iv) or at least partially in parallel with step iv), pulling the injured ligament to the bone with the bone opening, and fixing the ligament to the bone by tying a knot in the suture of the at least one suture anchor between the bone and a dorsal side of the injured ligament;
wherein the at least one suture anchor comprises a material having thermoplastic properties and is anchored in the bone opening with the aid of vibratory energy used for in situ liquefaction of the material having thermoplastic properties.

2. The method according to claim 1, wherein the injured ligament is selected from the group consisting of: a volar plate, a collateral ligament of the interphalangeal joints of the foot, a collateral ligament of metatarsophalangeal joints, a first intermetacarpal ligament, a syndesmosis ligament and a plantar calcaneonavicular ligament.

3. The method according to claim 1, wherein threading two ends of the suture through the injured ligament includes passing the suture through the injured ligament in a direction from outside of the joint towards the joint.

4. The method according to claim 1, wherein step i) comprises: performing a longitudinal dorsal, lateral or medial incision to expose a joint.

5. The method according to claim 1, wherein there is no need to pull the at least one anchor tight.

6. The method according to claim 1, wherein the at least one anchor is fully made of a bio-degradable material.

7. The method according to claim 1, wherein the at least one anchor is placed outside an articular surface.

8. The method according to claim 1, wherein the knot is placed outside an articular surface.

9. The method according to claim 1, wherein the method comprises:
inserting at least two suture anchors, each into a separate bone opening and anchoring the at least two suture anchors, wherein the at least two suture anchors include the at least one suture anchor,
threading two ends of a suture of each anchored suture anchor through the injured ligament,
pulling the injured ligament to the bone and fixing the injured ligament to the bone by tying a knot in each suture.

10. The method according to claim 1, wherein the suture is attached to the anchored at least one suture anchor before step iv) is carried out.

* * * * *